US006591664B2

(12) United States Patent
Litton

(10) Patent No.: US 6,591,664 B2
(45) Date of Patent: Jul. 15, 2003

(54) METHOD AND ARRANGEMENT FOR MEASURING CHARACTERISTICS OF A NON-NEWTONIAN FLUID

(75) Inventor: Jan-Eric Litton, Stockholm (SE)

(73) Assignee: Viscocheck AB, Stockholm (SE)

( * ) Notice: Subject to any disclaimer, the term of this patent is extended or adjusted under 35 U.S.C. 154(b) by 0 days.

(21) Appl. No.: 10/034,187

(22) Filed: Jan. 3, 2002

(65) Prior Publication Data
US 2002/0124634 A1 Sep. 12, 2002

Related U.S. Application Data

(63) Continuation of application No. PCT/SE00/01458, filed on Jul. 7, 2000.

(30) Foreign Application Priority Data

Jul. 7, 1999 (SE) .............................................. 9902613

(51) Int. Cl.[7] ........................ G01N 11/12; G01N 11/10; G01N 11/16
(52) U.S. Cl. .................... 73/54.41; 73/54.01; 73/54.27
(58) Field of Search ............................. 73/54.41, 54.26, 73/54.27, 54.31, 54.01

(56) References Cited

U.S. PATENT DOCUMENTS

| 2,679,157 A | * | 5/1954 | Carpenter | 73/59 |
| 3,449,940 A | * | 6/1969 | Banks | 73/32 |
| 3,712,117 A |   | 1/1973 | Fitzgerald et al. | 73/59 |
| 3,875,791 A | * | 4/1975 | Fitzgerald et al. | 73/59 |
| 3,965,722 A | * | 6/1976 | Bagg et al. | 73/59 |
| 4,154,093 A | * | 5/1979 | Smith et al. | 73/54 |
| 4,625,565 A | * | 12/1986 | Wada et al. | 73/861.74 |
| 4,643,021 A |   | 2/1987 | Mattout | 73/59 |
| 4,864,849 A | * | 9/1989 | Wright | 73/57 |
| 5,394,739 A | * | 3/1995 | Garvey, III et al. | 73/54.23 |
| 6,018,988 A | * | 2/2000 | Persson | 73/54.25 |
| 6,035,703 A | * | 3/2000 | Abnett | 73/54.01 |
| 6,247,354 B1 | * | 6/2001 | Vig et al. | 73/54.41 |
| 6,378,357 B1 | * | 4/2002 | Han et al. | 73/54.41 |

FOREIGN PATENT DOCUMENTS

| RU | 1821129 | 6/1993 |
| WO | WO86/00408 | 1/1986 |

* cited by examiner

Primary Examiner—Helen Kwok
Assistant Examiner—David Wiggins
(74) Attorney, Agent, or Firm—Pennie & Edmonds LLP

(57) ABSTRACT

To measure characteristics of a non-Newtonian fluid, preferably blood, a non-magnetic container is provided for receiving the fluid. A magnetic body is contained in the container, and a winding is provided around the container. An AC current supplying device is connected to the winding for supplying input AC current of different amplitudes thereto to generate magnetic fields of different strengths in the container to cause the magnetic body to oscillate at different shear rates in the fluid. A measuring device is provided for measuring amplitude and/or phase of the oscillations of the magnetic body and a shear rate determining device is provided for determining the shear rates by measuring differences between the amplitude and/or phase of the oscillations of the magnetic body and the amplitude and phase of the input AC currents. The amplitude difference at a specific shear rate is proportional to the viscosity of the fluid, and the phase difference at a specific shear rate is proportional to the viscoelasticity of the fluid.

8 Claims, 1 Drawing Sheet

METHOD AND ARRANGEMENT FOR MEASURING CHARACTERISTICS OF A NON-NEWTONIAN FLUID

RELATED APPLICATIONS

This is Continuation under 35 USC §120 of the U.S. National Stage Designation of PCT/SE00/01458, filed Jul. 7, 2000.

TECHNICAL FIELD

The invention relates generally to measurement of characteristics of a non-Newtonian fluid and more specifically to a method and an arrangement for measuring viscoelasticity of a non-Newtonian fluid, particularly blood.

BACKGROUND OF INVENTION

Blood viscosity and viscoelasticity are missing or at least overlooked factors in health care. One of the leading causes of death in the western world is formation of blood clot (thrombus) in a blood vessel. The more viscous the human blood is, the greater the risk is of developing vessel damage that can lead to a heart attack or a stroke. Mounting evidence indicates that the blood viscosity is elevated among patients with essential hypertension and that blood stickiness is an early development of atherosclerosis. Viscoelasticity of blood is associated with pathologies such as peripheral vascular disease and diabetes.

Blood viscosity and viscoelasticity are low at high shear rates. However, low shear rates arise at sites of atherogenesis, thrombogenesis, and ischaemia, promoting local hyperviscosity. This suggests that abnormalities in haemorheological factors be involved in the complication of hypertension and determination of blood pressure.

Blood is a suspension of mostly elastic particles, i.e. cells, in a Newtonian fluid, i.e. plasma, which results in non-Newtonian characteristics in that whole blood viscosity and viscoelasticity are dependent upon the shear rate the blood experiences.

U.S. Pat. No. 4,643,021 discloses a method and apparatus for measuring the viscosity of biological fluids, e.g. blood, by means of a rotating cylinder immersed in the fluid in a tube and on the basis of a torque applied to the cylinder and the speed of rotation of the cylinder. The cylinder is rotated by a rotating electromagnetic field produced by an induction winding that coaxially surrounds the tube and the cylinder and that is powered with current at an adjustable intensity.

The method disclosed in the above U.S. Pat. No. 4,643,021, utilizing a rotating cylinder, is not sensitive enough for measuring deformation of red blood cells and, consequently, it is not possible to measure viscoelasticity of e.g. blood by means of that method.

SUMMARY OF THE INVENTION

The object of the invention is to bring about a simple and inexpensive method and arrangement enabling measurement of viscosity and viscoelasticity of non-Newtonian fluids, particularly blood.

This is attained by the method according to the invention in that the fluid is received in a non-magnetic container containing a magnetic body, a winding is provided around the container, input AC currents of different amplitudes are supplied to the winding to generate magnetic fields of different strengths in the container to cause the magnetic body to oscillate at different shear rates in the fluid, amplitude and/or phase of the oscillations of the magnetic body are measured, and the shear rates are determined by measuring differences between the amplitude and/or phase of the oscillations of the magnetic body and the amplitude and phase of the input AC currents, the amplitude difference at a specific shear rate being proportional to the viscosity of the fluid, and the phase difference at a specific shear rate being proportional to the viscoelasticity of the fluid.

The object is also attained by means of the arrangement according to the invention, comprising a non-magnetic container for receiving the fluid, a magnetic body being contained in the container, a winding being provided around the container, an AC current supplying device being connected to the winding for supplying input AC current of different amplitudes thereto to generate magnetic fields of different strengths in the container to cause the magnetic body to oscillate at different shear rates in the fluid, a measuring device being provided for measuring amplitude and/or phase of the oscillations of the magnetic body, and a shear rate determining device being provided for determining the shear rates by measuring differences between the amplitude and/or phase of the oscillations of the magnetic body and the amplitude and/or phase of the input AC currents, the amplitude difference at a specific shear rate being proportional to the viscosity of the fluid, and the phase difference at a specific shear rate being proportional to the viscoelasticity of the fluid.

By means of the method and the arrangement according to the invention, e.g. clinical measurements of blood viscoelasticity will be possible, simply using a single blood sample.

DESCRIPTION OF THE DRAWINGS

The invention will be described in more detail below with reference to the appended drawings, in which.

DETAILED DESCRIPTION OF THE INVENTION

Even if the following description is particularly directed to measuring viscosity and viscoelasticity of blood, it is to be understood that the description is equally valid for any non-Newtonian fluid, such as saliva and thixotropic fluids in general.

Figure 1:
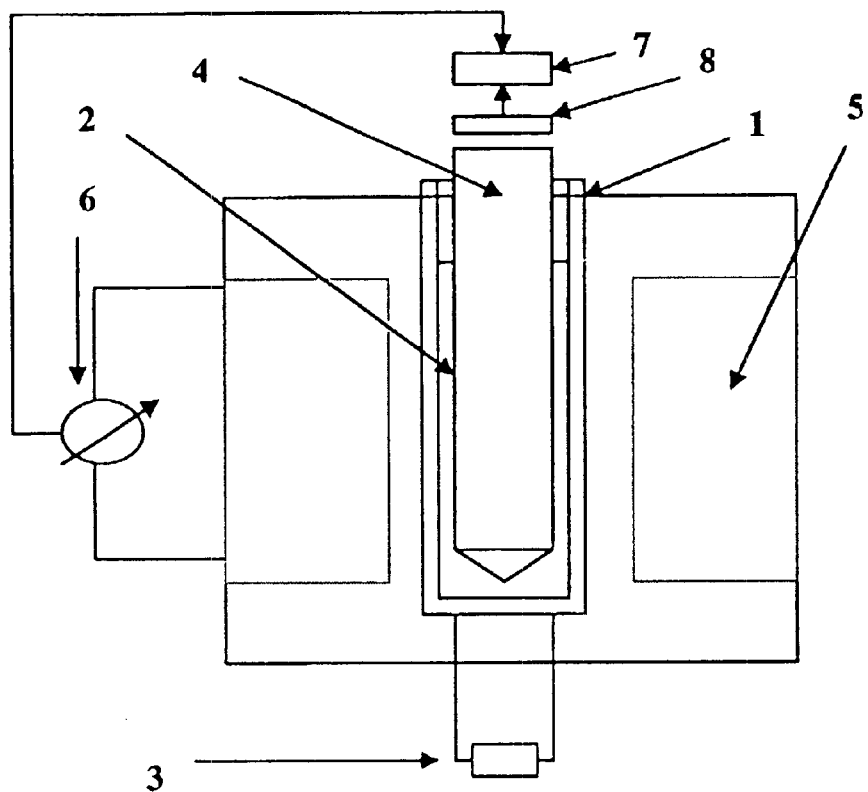
FIG. 1 illustrates an embodiment of an arrangement in accordance with the invention for measuring viscoelasticity of blood.

FIG. 1 illustrates an embodiment of an arrangement in accordance with the invention, for measuring viscosity and viscoelasticity of blood.

The arrangement illustrated in FIG. 1 comprises a container 1 of a non-magnetic material, which is filled with a small volume blood sample 2. In the embodiment illustrated in FIG. 1, the container 1 is a test tube.

When measuring the viscosity and viscoelasticity of blood, it is necessary to thermostabilize the container 1 at a temperature of 37 C. by means of a thermostabilizing device 3 known per se.

A magnetic body 4, shown as a cylinder in FIG. 1, is located in the container 1 to freely float in the blood sample 2. A winding 5 connected to an input AC current supplying device 6 is provided around the container 1.

In accordance with the invention, the current supplying device 6 is adapted to supply input AC currents of different amplitudes to the winding 5 to generate magnetic fields of different strengths in the container 1 to cause the magnetic body 4 to oscillate at different shear rates in the blood sample 2 in the container 1.

In accordance with the invention, the AC currents are supplied at a fixed low frequency, preferably lower than 10 Hz.

To determine the shear rate of the magnetic body 4 at the different amplitudes of the AC current, a shear rate determining device 7 is provided. The shear rate determining device 7 is connected with one input to a measuring device 8 that is adapted to measure the amplitude and/or phase of the oscillations of the magnetic body 4 in the blood sample 2 in the container 1, and with another input to the input AC current supplying device 6.

The shear rate determining device 7 is adapted to compare the amplitude and/or phase of the oscillations of the magnetic body 4 measured by the measuring device 8 with the amplitude and/or phase of the input AC current provided to the winding 5 by the current supplying device 6 at different amplitudes of the input AC current, and to determine the differences.

The amplitude difference is proportional to the viscosity of the fluid, and the phase difference is proportional to the viscoelasticity of the fluid.

The measuring device 8 is preferably a contactless device, e.g. an optical or magnetical device. In order for such a measuring device 8 to be able to determine the amplitude and/or phase of the oscillations of the magnetic body 4, the magnetic body 4 is provided with means (not shown) that are optically or magnetically readable or detectable.

By supplying input AC currents of different amplitudes to the winding 5, the viscosity and the viscoelasticity of the blood sample 2 in the container 1 can be determined by the shear rate determining device 7 at different shear rates.

Figure 2:
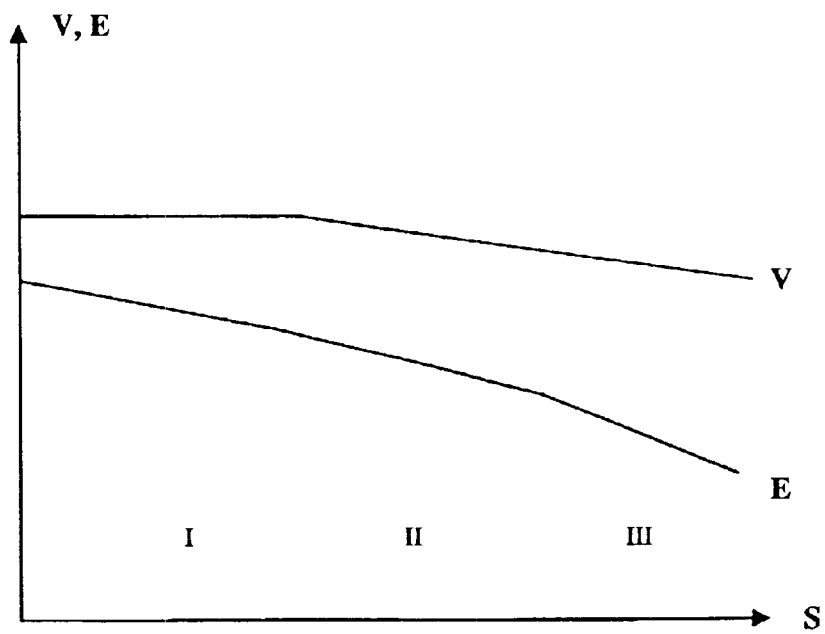
FIG. 2 is a diagram showing the relationships between blood viscosity and shear rate as well as between blood viscoelasticity and shear rate.

On the basis hereof, curves of viscosity and viscoelasticity versus shear rate can be constructed as illustrated in FIG. 2. In FIG. 2, V represents the viscosity at different shear rates S, while E represents the viscoelasticity at different shear rates S.

A scan with increasing shear rates S according to FIG. 2 shows influences of aggregation of red blood cells (region I in FIG. 2), disaggregation of red blood cells (region II in FIG. 2), and deformation of red blood cells (region III in FIG. 2).

In accordance with the invention, the container 1 may be a test tube or even a syringe (not shown), provided in advance with a small magnetic body corresponding to the magnetic body 4 in FIG. 1.

In case of a syringe, a blood sample can be drawn from a patient by means of such a syringe. The syringe is then placed in the centre hole of a winding in order to measure the viscosity and/or viscoelasticity of the blood in the syringe.

As should be apparent from the above, a simple device suitable for clinical measurement of blood viscosity and/or viscoelasticity is obtained in accordance with the invention.

What is claimed is:

1. A method of measuring viscoelasticity of a non-Newtonian fluid comprising:
   providing a non-magnetic container surrounded by a winding, the non-magnetic container containing a magnetic body;
   supplying AC currents to the winding to cause the magnetic body to oscillate at different shear rates in the fluid; and
   optically measuring phase differences between the supplied AC currents and the resulting oscillations of the magnetic body to determine the viscoelasticity of the fluid within an interval, the phase difference at each shear rate being proportional to the viscoelasticity of the fluid at that shear rate.

2. The method as claimed in claim 1, comprising the steps of:
   supplying the input AC currents at a fixed low frequency; and
   measuring the phase of the oscillations of the magnetic body optically.

3. A method of measuring characteristics of a non-Newtonian fluid, comprising:
   providing a non-magnetic container having a winding therearound and a magnetic body therein;
   receiving a non-Newtonian fluid into the non-magnetic container;
   supplying input AC currents of different amplitudes to the winding to generate magnetic fields of different strengths in the container to cause the magnetic body to oscillate at different shear rates in the fluid,
   optically measuring at least one of amplitudes and phases of the oscillations of the magnetic body;
   determining shear rates of the non-Newtonian fluid by measuring differences between amplitudes and/or phases of the oscillations of the magnetic body and the amplitudes and/or phases of the input AC currents, the amplitude difference at a specific shear rate being proportional to the viscosity of the fluid, and the phase difference at a specific shear rate being to the viscoelasticity of the fluid.

4. The method as claimed in claim 3, comprising the step of supplying the input AC currents at a fixed low frequency.

5. An arrangement for measuring viscoelasticity of a non-Newtonian fluid comprising:
   a non-magnetic container surrounded by a winding, the non-magnetic container containing a magnetic body,
   an AC current supplying device connected to the winding for supplying AC currents thereto to cause the magnetic body to oscillate at different shear rates in the fluid;
   a measuring device adapted to optically measure phase differences between the supplied AC currents and the resulting oscillations of the magnetic body to determine the viscoelasticity of the fluid within an interval, the phase difference at each shear rate being proportional to the viscoelasticity of the fluid at that shear rate.

6. The arrangement as claimed in claim 5, wherein the AC current supplying device is adapted to supply the input AC currents at a fixed low frequency.

7. An arrangement for measuring characteristics of a non-Newtonian fluid, comprising:
   a non-magnetic container for receiving the fluid,
   a magnetic body being contained in the container, and
   a winding provided around the container,
   an AC current supplying device connected to the winding for supplying input AC current of different amplitudes thereto to generate magnetic fields of different strengths in the container to cause the magnetic body to oscillate at different shear rates in the fluid;
   a measuring device adapted to optically measure amplitude and/or phase of the oscillations of the magnetic body, and
   a shear rate determining device for determining the shear rates by measuring differences between the amplitude and/or phase of the oscillations of the magnetic body and the amplitude and/or phase of the input AC currents, the amplitude difference at a specific shear rate being proportional to the viscosity of the fluid, and the phase difference at a specific shear rate being proportional to the viscoelasticity of the fluid.

8. The arrangement as claimed in claim 7, wherein the AC current supplying device is adapted to supply the input AC currents at a fixed low frequency.

* * * * *

UNITED STATES PATENT AND TRADEMARK OFFICE
CERTIFICATE OF CORRECTION

PATENT NO.    : 6,591,664 B2
DATED         : July 15, 2003
INVENTOR(S)   : Jan-Eric Litton It is certified that error appears in the above-identified patent and that said Letters Patent is hereby corrected as shown below:

<u>Column 4,</u>
Line 22, insert the term -- proportional -- after the word "being".

Signed and Sealed this

Fourth Day of November, 2003

JAMES E. ROGAN
*Director of the United States Patent and Trademark Office*